(12) United States Patent
Patmore et al.

(10) Patent No.: US 10,830,753 B2
(45) Date of Patent: Nov. 10, 2020

(54) COMPOSITE MATERIAL WITH FAILURE DETECTION PROPERTIES

(71) Applicant: Stryker Corporation, Kalamazoo, MI (US)

(72) Inventors: Kevin M. Patmore, Plainwell, MI (US); Andrew M. Bentz, Kalamazoo, MI (US); Brett M. Fulton, Andover, MA (US); Sarah E. Mynhier, Seattle, WA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 16/112,027

(22) Filed: Aug. 24, 2018

(65) Prior Publication Data

US 2019/0056377 A1 Feb. 21, 2019

Related U.S. Application Data

(63) Continuation of application No. 14/972,994, filed on Dec. 17, 2015, now Pat. No. 10,060,902.
(Continued)

(51) Int. Cl.
*G01N 33/44* (2006.01)
*G01M 3/00* (2006.01)
(Continued)

(52) U.S. Cl.
CPC ............ *G01N 33/442* (2013.01); *G01M 3/00* (2013.01); *G01M 3/042* (2013.01); *G01M 3/045* (2013.01);
(Continued)

(58) Field of Classification Search
CPC ....... G01N 33/442; G01N 33/44; G01M 3/00; G01M 3/042; G01M 3/04; G01M 3/02
(Continued)

(56) References Cited

U.S. PATENT DOCUMENTS

| 4,538,311 A | 9/1985 | Hall et al. |
| 4,704,108 A | 11/1987 | Okada et al. |

(Continued)

FOREIGN PATENT DOCUMENTS

| CA | 2094279 C | 4/1999 |
| CN | 101103268 A | 1/2008 |

(Continued)

OTHER PUBLICATIONS

International Search Report for PCT/US2015/066377, the international counterpart to U.S. Appl. No. 14/972,994 dated Apr. 29, 2016.
(Continued)

*Primary Examiner* — Christine T Mui
(74) *Attorney, Agent, or Firm* — Warner Norcross + Judd LLP

(57) ABSTRACT

A multiple layer composite material having fluid breach detection features provides indication of a failure in a fluid barrier. The indication of breach of fluid is provided before failure of a final layer of the composite material. The multiple layer composite material includes more than one fluid impermeable layer with an intermediate layer sealed between the fluid impermeable layers. Failure of one of the fluid impermeable layers is detected by fluid contact in the intermediate layer. The intermediate layer includes a reagent and/or detection device to indicate that the fluid has reached the intermediate layer.

17 Claims, 7 Drawing Sheets

Related U.S. Application Data

(60) Provisional application No. 62/094,571, filed on Dec. 19, 2014.

(51) Int. Cl.

| | | |
|---|---|---|
| *G01N 15/08* | (2006.01) | |
| *G01N 21/88* | (2006.01) | |
| *G01M 3/04* | (2006.01) | |
| *G01N 21/78* | (2006.01) | |
| *G01N 27/12* | (2006.01) | |
| *G01N 21/77* | (2006.01) | |
| *G01N 21/84* | (2006.01) | |
| *G01N 21/80* | (2006.01) | |

(52) U.S. Cl.
CPC ............ *G01M 3/047* (2013.01); *G01N 15/08* (2013.01); *G01N 15/0826* (2013.01); *G01N 21/78* (2013.01); *G01N 21/8803* (2013.01); *G01N 27/12* (2013.01); *G01N 21/80* (2013.01); *G01N 2015/086* (2013.01); *G01N 2015/0846* (2013.01); *G01N 2021/7796* (2013.01); *G01N 2021/8472* (2013.01)

(58) Field of Classification Search
USPC .......................................................... 116/206
See application file for complete search history.

(56) References Cited

U.S. PATENT DOCUMENTS

| | | | |
|---|---|---|---|
| 4,826,479 A | | 5/1989 | Burgin et al. |
| 4,935,260 A | * | 6/1990 | Shlenker ................ A61B 42/10 604/349 |
| 5,045,341 A | * | 9/1991 | Shlenker ................ A61B 42/10 128/844 |
| 5,058,088 A | | 10/1991 | Haas et al. |
| 5,064,440 A | | 11/1991 | Howard et al. |
| 5,135,792 A | | 8/1992 | Hogan |
| 5,335,373 A | * | 8/1994 | Dresdner, Jr. .......... A61B 42/10 2/161.7 |
| 5,364,132 A | | 11/1994 | Haas et al. |
| 5,446,705 A | | 8/1995 | Haas et al. |
| 5,549,924 A | | 8/1996 | Shlenker et al. |
| 5,602,804 A | | 2/1997 | Haas |
| 5,603,161 A | | 2/1997 | Welsh |
| 5,633,835 A | | 5/1997 | Haas et al. |
| 5,699,326 A | | 12/1997 | Haas et al. |
| 5,715,215 A | | 2/1998 | Haas et al. |
| 5,719,828 A | | 2/1998 | Haas et al. |
| 5,785,354 A | | 7/1998 | Haas |
| 5,862,101 A | | 1/1999 | Haans et al. |
| 5,873,606 A | | 2/1999 | Haas et al. |
| 5,923,001 A | | 7/1999 | Morris et al. |
| 5,930,206 A | | 7/1999 | Haans et al. |
| 5,957,458 A | | 9/1999 | Haas et al. |
| 6,026,818 A | | 2/2000 | Blair et al. |
| 6,390,908 B1 | | 5/2002 | Chen et al. |
| 6,452,873 B1 | | 9/2002 | Holt et al. |
| 6,778,090 B2 | | 8/2004 | Newham |
| 6,796,096 B1 | | 9/2004 | Heath |
| 7,008,310 B2 | | 3/2006 | Andres |
| 7,120,952 B1 | | 10/2006 | Bass et al. |
| 7,784,508 B2 | | 8/2010 | Kemp et al. |
| 8,050,814 B2 | | 11/2011 | Rains et al. |
| 8,501,103 B2 | * | 8/2013 | Bangera ............... G08B 21/245 422/117 |
| 8,715,248 B2 | | 5/2014 | McKinnon |
| 8,747,775 B2 | | 6/2014 | Sandvick |
| 8,870,083 B2 | | 10/2014 | Myers et al. |
| 8,939,379 B2 | | 1/2015 | Myers et al. |
| 2003/0006762 A1 | | 1/2003 | Clements |
| 2004/0191118 A1 | | 9/2004 | Mody |
| 2006/0241399 A1 | | 10/2006 | Fabian |
| 2007/0125392 A1 | | 6/2007 | Olson, Jr. et al. |
| 2007/0247318 A1 | | 10/2007 | Pempsell et al. |
| 2007/0285249 A1 | | 12/2007 | Blair et al. |
| 2009/0012418 A1 | | 1/2009 | Gerlach |
| 2009/0301382 A1 | | 12/2009 | Patel |
| 2010/0190004 A1 | | 7/2010 | Gibbins et al. |
| 2012/0135527 A1 | | 5/2012 | Bangera et al. |
| 2016/0294040 A1 | | 10/2016 | Blair |

FOREIGN PATENT DOCUMENTS

| | | |
|---|---|---|
| DE | 69511563 T2 | 3/2000 |
| JP | 57101737 A | 6/1982 |
| JP | 06280499 A | 10/1994 |
| JP | 10281918 A | 10/1998 |
| JP | 2001115607 A | 4/2001 |
| JP | 2008082716 A | 4/2008 |
| WO | 9839164 A1 | 9/1998 |
| WO | 9853984 A1 | 12/1998 |
| WO | 0111332 A2 | 2/2001 |

OTHER PUBLICATIONS

International Written Opinion for PCT/US2015/066377, the international counterpart to U.S. Appl. No. 14/972,994 dated Apr. 29, 2016.

\* cited by examiner

COMPOSITE MATERIAL WITH FAILURE DETECTION PROPERTIES

CROSS REFERENCE TO RELATED APPLICATIONS

This application is a continuation of U.S. patent application Ser. No. 14/972,994, filed Dec. 17, 2015, entitled COMPOSITE MATERIAL WITH FAILURE DETECTION PROPERTIES, now U.S. Pat. No. 10,060,902, which claims benefit of U.S. provisional App. Ser. No. 62/094,571, filed Dec. 19, 2014, which are incorporated by reference in their entireties herein.

BACKGROUND OF THE INVENTION

The present invention relates to a multiple layer composite material including features for detection of a failure in one or more layers resulting in a fluid breach of the composite material. The composite material is suitable for use as a barrier in many applications where fluid penetration is undesired.

Impermeable covers are intended to protect areas, objects, or people from coming into contact with a fluid. These covers have been made from flexible fabric with a flexible fluid proof coating such as polyvinyl chlorides ("PVCs") or polyurethanes. Over time, the coatings lose their ability to bar entry of a fluid into the protected area, or onto protected objects or people.

These covers are known to fail as barriers in a number of ways. Some failure modes are obvious, such as large cracks or tears in the cover, or a visible delamination of the coating. Other failure modes are less observable. Current methods of inspection of a barrier material for integrity are reactive and identify a failure only after fluid has breached the barrier.

SUMMARY OF THE INVENTION

Accordingly, the present invention provides an improved composite material having multiple layers with failure detection features for detecting breach of fluid into the composite material before the final layer is breached. Additionally, the composite material is useful in a variety of applications as a barrier material.

One embodiment provides a multiple layer composite material with a first fluid impermeable layer, a second fluid impermeable layer, and an intermediate layer sealed between the first and second fluid impermeable layers. The intermediate layer includes a reagent that is reactive when a fluid contacts the reagent after having passed through the first or second fluid impermeable layers.

In one aspect, the reagent is visibly detectable when the fluid contacts the reagent.

In another aspect, conductive elements are in fluid communication with the reagent. The reagent is a variable conductivity material that conducts electric current in the electric circuit after contact with the fluid.

In one aspect, the reagent is reactive to a cleaning fluid applied to the first fluid permeable layer.

In any of the foregoing embodiments, the intermediate layer is impregnated with a pattern of reagent, and the first fluid impermeable layer is translucent. The pattern is visible through the first fluid impermeable layer after the fluid passes through the first fluid impermeable layer.

In one aspect, the reagent releases a fragrant substance when reacting to the fluid.

In another embodiment, the composite material with breach detection properties has a first fluid impermeable layer, a second fluid impermeable layer, and an intermediate layer sealed between the first and second fluid impermeable layers. The intermediate layer has a plurality of fibers with an alterable characteristic. The characteristic is alterable after contact with a fluid after the fluid passes through the first or second fluid impermeable layer.

In another embodiment, the multiple layer material with breach detection properties has a first fluid impermeable layer, a second fluid impermeable layer, and an intermediate layer sealed between the first and second fluid impermeable layers. The intermediate layer has a detector that indicates a status of the material.

In another embodiment, the multiple layer material with breach detection properties has a first fluid impermeable layer, a second fluid impermeable layer, and an intermediate layer sealed between the first and second fluid impermeable layers. Both a positive terminal and a negative terminal are associated with the intermediate layer.

In one aspect, the positive terminal and the negative terminal are connected to a detector that is operable to determine a status of the material.

Any of the foregoing embodiments may provide the composite material as a barrier for a mattress cover, a protective garment, a glove, a rain coat, a handle, a seat, or a pad.

In one embodiment, a method of manufacturing a composite material with breach detection properties is provided. The method includes the steps of: providing a first fluid impermeable layer, providing a second fluid impermeable layer, providing an intermediate layer having a breach detector therein, and sealing the intermediate layer between the first and second fluid impermeable layers.

In another embodiment, a method of detecting a breach in a composite material is provided. The method comprising the steps of: providing a first fluid impermeable layer, providing a second fluid impermeable layer, providing an intermediate layer, providing a breach detection component in the intermediate layer, sealing the intermediate layer between the first and second fluid impermeable layers, and observing a change in the breach detection component after a fluid passes through the first impermeable layer.

Further, the above embodiments may include the multiple layer composite material having a first outer fluid impermeable layer, a second outer fluid impermeable layer opposite said first outer impermeable layer, an inner fluid impermeable layer having a reagent, and an inner reinforcement layer. The inner fluid impermeable layer and the inner reinforcement layer are sealed between the first outer fluid impermeable layer and said second outer impermeable layer. The reagent is active with a fluid when the fluid contacts the reagent after passing through the first outer fluid impermeable layer or the second outer fluid impermeable layer.

These and other objects, advantages, and features of the invention will be more fully understood and appreciated by reference to the description of the current embodiment and the drawings.

Figure 1:
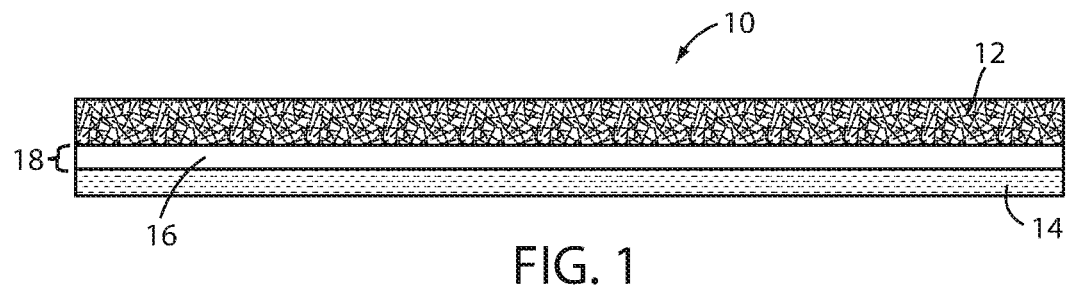
FIG. 1 is a schematic diagram of a multiple layer composite material.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and may be practiced or carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DESCRIPTION OF THE EMBODIMENTS

Composite Material

Referring to FIG. 1, a multiple layer composite material, generally designated as 10, is illustrated. The material includes a first fluid impermeable layer 12, a second fluid impermeable layer 14, and an intermediate layer 16 within an internal space 18 defined by the first fluid impermeable layer 12 and the second fluid impermeable layer 14. The intermediate layer 16 may be sealed between the first fluid impermeable layer 12 and the second fluid impermeable layer 14. The intermediate layer 16 includes a reagent that is active with a fluid when the fluid contacts the reagent after passing through the first fluid impermeable layer 12 or the second fluid impermeable layer 14.

The material 10 provides a fluid barrier between an environment and an area, object, or person intended to remain void of contact with the fluid. One of the fluid impermeable layers 12, 14 may be a bottom layer in contact with the area, object, or person intended to be separated from the fluid. The other fluid impermeable layer 12, 14 may be a top layer opposite the bottom layer. A failure in the top layer of the composite material provides an opening for fluid to enter the composite material. Once the fluid enters the internal space 18 and interacts with the reagent of the intermediate layer 16, the failure of the top impermeable layer and breach of fluid into the composite material can be detected before failure of the bottom layer. In this way, the bottom layer acts as a final layer of protection preventing fluids to pass through the composite material and allowing the overall integrity of the barrier to remain intact. The composite material may then be replaced to restore the failure detection features.

Figure 2:
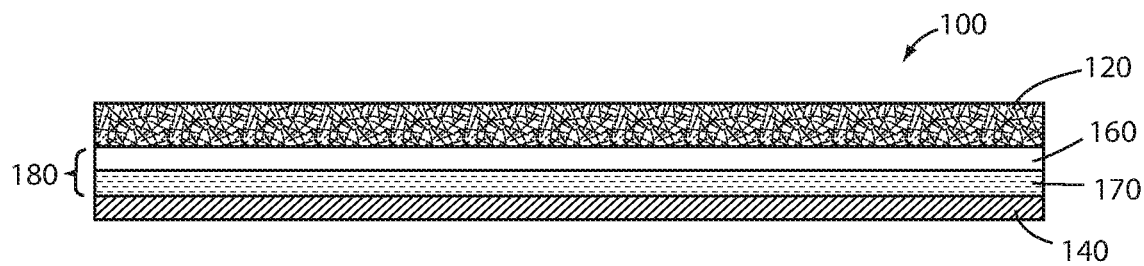
FIG. 2 is a second schematic diagram of a second embodiment of a multiple layer composite material.

Another embodiment of the multiple layer composite material is shown in FIG. 2. The multiple layer composite material 100 may include a first outer fluid impermeable layer 120 and a second outer fluid impermeable layer 140 opposite the first outer impermeable layer 120. An inner layer 160 having a reagent and an inner reinforcement layer 170 may be positioned within the internal space 180 defined by the first outer fluid impermeable layer 120 and the second outer fluid impermeable layer 140. The inner layer 160 and the inner reinforcement layer 170 may be sealed between the first outer fluid impermeable layer 120 and the second outer impermeable layer 140. The reagent can be activated with a fluid when the fluid contacts the reagent after passing through the first outer fluid impermeable layer 120 or the second outer fluid impermeable layer 140.

The composite materials are suitable for use in a variety of applications where a barrier material is useful or desired. By way of example only, the composite materials may be constructed for use as a mattress cover, protective garment, glove, rain coat, barrier on a handle or seat, or a pad for use in fluid barrier applications. When used in any application, the multiple layer composite materials 10, 100 may be disposable once fluid has been detected as having passed through the first fluid impermeable layer 12, 120 or second fluid impermeable layer 14, 140.

The fluid impermeable layers may be the outermost layers of the composite material or may be layers within a construction having additional layers. The fluid impermeable layers may be constructed of flexible fabric structure with a flexible fluid proof coating. For example, polyvinyl chlorides ("PVC") or polyurethanes are suitable. Extruded, rolled, dipped polymers, or polymers that are formed into sheets of material, are also suitable for use as the fluid impermeable layers. The intermediate layer may be constructed of synthetic or natural fabric, extruded, woven, unwoven, and/or reinforced materials.

Figure 3:
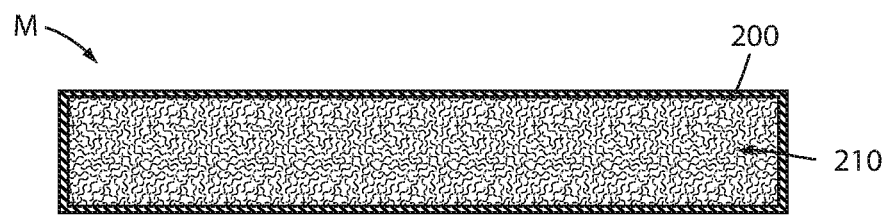
FIG. 3 is a schematic diagram of a mattress and cover of multiple layer composite material.

As shown in FIG. 3, if the composite material 10, 100 is used as a mattress cover, the cover 200 may surround the internal components 210 of a mattress M. It may be desirable to protect the internal components 210 of the mattress M from fluid contamination in order to avoid spoiling of the internal components 210 and/or to avoid the spread of pathogens in fluid that could be deposited on the mattress M. The cover 200 can be placed on or around the mattress M, and a breach of fluid through a fluid impermeable layer of composite material may be detected and/or avoided by any of the features described herein.

Failures of an impermeable layer resulting in fluid breach into the composite material may be directly observed after the fluid passes through the impermeable layer and reacts with a reagent. Meanwhile, the opposite impermeable layer may remain intact. Reagents may be selected from materials that exhibit a first color prior to contact with fluid and are capable of exhibiting a second, different color after contact with the fluid. Either the failed or intact fluid impermeable layer may be translucent to allow the color change to be readily observed from a vantage point outside the composite material.

The color change elicited by the reagent may be in response to one or more properties of the fluid that passed through the failed fluid impermeable layer. Additionally, or alternatively, more than one reagent may be associated with the intermediate layer 16, 160 and the reagents may individually react in various ways to indicate a particular type of fluid that has passed through the failed layer. For example, the wetness of the fluid may be indicated by a color change in one or more reagent. If a protein is present in the fluid, a reagent intended to detect the protein may change color. If the fluid passing through a fluid impermeable layer 12, 14, 120, 140 is expected to vary in pH, litmus mixture may be the reagent associated with the intermediate layer 16, 160, to provide an indication of the type of fluid that has entered the composite material. Reagents capable of changing color based on pKa values, the presence of fluids containing amino acids, proteins, urine, other bodily or biological fluids, or water may also be present in the intermediate layer 16, 160.

Reagents may include chemical indicators that change color as pH changes. Acid/base indicators may be visible as a first color under neutral conditions and visible as a second, different color at an acidic or basic pH. Two examples, Bromocresol Green (also known as 3',3", 5', 5"-tetrabromo-m-cresol-sulfonephthalein with a pK of 4.90) and Bromophenol Blue are blue at a neutral pH and transition through green to yellow as the pH decreases. Bromocresol Green transitions between pH values of about 5.4-3.8. Bromophenol Blue transitions between pH values of about 4.6-3.0. Another example is Phenolphthalein which is clear at a neutral pH and transitions to red-violet at the pH increases. Phenolophthalein transitions between pH values of about 8.0 to about 9.8. Other examples include, but are not limited to, litmus, Nitrazine Strips, Bromothymol Blue, Methyl Orange, and Yamada Universal Indicator.

Reagents that appear as one color when dry and a second, different color when wet can also be useful. For example, cobalt chloride is blue when dry and dark red when wet.

Reagents that luminesce may be desired if the composite material is intended for use in lower light settings. For example, some suitable chemiluminescence reagents may be diphenyl oxalate which, when combined with a weak base (e.g., 2,4,6-trichlorophenol) is responsible for the luminescence in a glow stick. Various colors may be produced depending upon the dye added. Other examples include lunimol, and fluorescein.

As with any chemical reaction, there are generally multiple components. The various compounds can be considered as to which chemical is embedded as a solid within the fabric, and which is suspended in the reacting fluid.

The reagent associated with the intermediate layer may be placed there or be impregnated in a pattern. For example, the fluid impermeable layer may be transparent so that the color change of the pattern is visible through one or both of the fluid impermeable layers after the fluid breaches one of these layers. The pattern may be individual or interlaced shapes or designs, or may be letters that spell out one or more words to indicate a breach in one of the fluid permeable layers.

Rather than change color, the reagent may produce foam upon, or after, contact with a fluid. The foam may then be detectable in a number of ways including, but not limited to, causing a change in the thickness of the composite material. The change in thickness may be localized to the area of material in which a breach of a fluid impermeable layer 12, 14, 120, 140 or may generate a more generalized thickening of the material 10, 100.

Further, the reagent associated with the intermediate layer 16, 160 may release a fragrant substance when reacting to the fluid. The fragrant substance may exit the internal space 18, 180 of the composite material 10, 100 through the breached area which could allow for detecting of the breach of a fluid impermeable layer 12, 14, 120, 140 by detecting a fragrance associated with the reaction between the fluid and the reagent.

Another example of a directly observable detection of a breach involves constructing the intermediate layer from a plurality of fibers having an alterable characteristic, or including a plurality of such fibers in the intermediate layer. The fiber characteristic can be alterable after contact with a fluid. For example, the fibers may be color alterable having a first color prior to contact with the fluid and a second, different color after contact with the fluid. Additionally, or alternatively, the alterable characteristic may be size. For example, prior to contact with the fluid the fibers are not detectable by touch, but after contact with the fluid, the fibers may increase in size so that they become detectable by touch.

As an alternative to, or in addition to, directly observable changes in the intermediate layer upon breach of a fluid through a fluid impermeable layer, another embodiment of the composite material includes one or more devices that allow detection of a breach in the material. For example, the intermediate layer may include a reagent that is a dielectric in the dry state, but becomes an electrolyte operable to conduct an electric current in an electric circuit after contact with the fluid. The reagent may be salt that will dissolve in the fluid and disassociate into anions, or negatively charged ions, and cations, or positively charged ions. The circuit further includes a power source, such as a battery cell, and a current sensor that detects the current in the circuit when the conductivity of the reagent changes.

Figure 4:
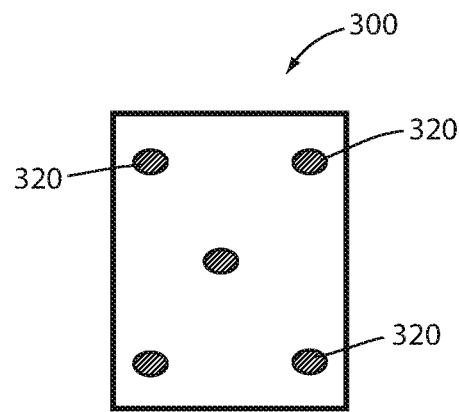
FIG. 4 is a schematic plan view of multiple layer composite material having a detection device.
Figure 5:
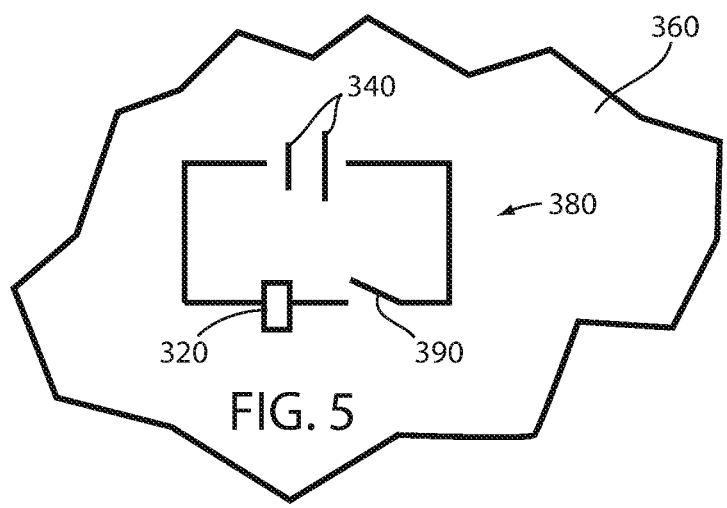
FIG. 5 is a circuit diagram for a detection device without a switch.

Referring now to FIGS. 4, and 5 the composite material 300 may include an indicator, such as a light emitting diode ("LED") 320, capable of indicating a breach of one of the fluid impermeable layers. Electric source 340 is in electric contact with the intermediate layer 360. The electric source is a part of an electrical circuit 380 including a material having a variable conductivity. The material transitions from a first state (e.g., non-conductive) to a second state (e.g. conductive) opposite the first state after the fluid breach of the material 300 and after moisturizing the material. The change in state of the material completes the circuit 380 as illustrated in FIG. 5. When the material changes states and completes the circuit, the LED 320 is powered to signal the breach. For example, the circuit 380 is open in dry state and closed in wet state by switch 390 (FIG. 5). By way of example, the reagent or material of variable conductivity may include salts containing one or more of sodium, potassium, magnesium, iron, ammonium, quaternary ammonium, calcium and one or more of chloride, acetate, carbonate, citrate, fluoride, nitrate, nitrite, sulfates, and phosphates. However, any suitable salt may be used. In addition to composite materials 10, 100 described earlier, the composite material 300 may also be used as the cover 200 surrounding the mattress M of FIG. 3.

It should be understood that the powered device need not be a light, but may be any other device capable for signaling a breach. Other devices may signal by, but not be limited to, an audible signal by an indicator capable of producing sound upon the change in state of the switch.

In composite materials having an intermediate layer with a plurality of optical fibers with an alterable characteristic, the characteristic may be a change in the total internal reflection properties of the fibers when moisture alters their optical properties. This change may then be detected, calculated or observed, for example, by observing the light extracted from the side walls of the fibers when the fibers are contacted by a fluid that disrupts total internal reflection in the fibers.

In addition to, or as an alternative to, providing an observable indication of a breach of the composite material, the breach may be detectable on inspection. For example, the reagent may be reactive to a cleaning material applied to one of the fluid impermeable layers if a breach in the impermeable layer is present. The cleaning material may be water or another cleaning material, such as ammonia solution, that is applied to the fluid impermeable layer during a routine cleaning session or may be applied at any time an inspection of the material is desired.

Another example of breach detection by inspection of the material may include providing at least one positive electrical terminal and at least one negative electrical terminal associated with said intermediate layer. During routine inspection, or when inspection is desired, the positive and negative terminals can be connected to a detector. The detector may be, for example, an interrogator and may be operable to determine a status of the material based on whether an electrical current or other signal is measured by the detector. For example, if an electrolyte of the intermediate layer is dissolved by a fluid, the detector may sense an electrical current when the terminals are connected to it. The detector may further be in communication with a display device and the status of the material may be indicated on the display device. If the composite material is a pad for a mattress, or if the composite material is incorporated into a mattress, the status of the material may be periodically checked and displayed by first communicating the status of the material to the mattress and then communicating the material status from the mattress to a bed having monitoring and display features. Alternatively, the material status may be checked and communicated directly to a bed with monitoring and display features such as those disclosed in U.S. patent application Ser. No. 13/836,813, titled "Inflatable mattress and control means" filed on Mar. 15, 2013 and incorporated herein by reference in its entirety. Multiple layer composite materials may also be provided with integrated devices for avoiding or safeguarding against a complete failure or breach in the composite material. In those instances, the intermediate layer may include a detector capable of directly indicating the status of the material. The detector may be operable to communicate a status of the material. The status may be indicated as new, active, or change. New status may indicate that the composite material has recently been installed or placed for use. Active status may be used to indicate that composite material is expected to be functioning properly and/or no breach in a fluid impermeable layer is expected or detected. Change status may be used to indicate that the material should be replaced due to time of use, level of use, or indicated breach of a fluid impermeable layer. For example, a timer may be included in the composite material to measure the length of time the material has been in use. A maximum time may be set for the use of the material and once the time limit is exceeded, the detector may signal for inspection, removal, or replacement of the composite material.

Age or wear of the composite material may also be measured by one or more sensors included in the intermediate layer. The sensors can be set to detect a threshold level of movement of the composite material. The number of threshold movements may be sensed and counted by a counter. Once a maximum number of threshold movements has been detected, the counter can communicate the event may be sent to a communications component, such as a radio frequency identification ("RFID") tag, and/or display device to indicate a status change. An example of a determining use by age or wear may include providing pressure sensors in an array in the intermediate layer and reading a pressure map as an indication of wear and use. The use or wear may be detected by pressure sensing array incorporated into a flexible sheet within the composite material. Examples of pressure sensing sheets or mats are described U.S. patent application Ser. No. 14/019,089 filed Sep. 5, 2013, U.S. patent application Ser. No. 14/341,328 filed Jul. 25, 2014, and PCT International Application No. PCT/US2012/027402 filed Mar. 2, 2012, all incorporated by reference herein in their entirety.

Figure 6:
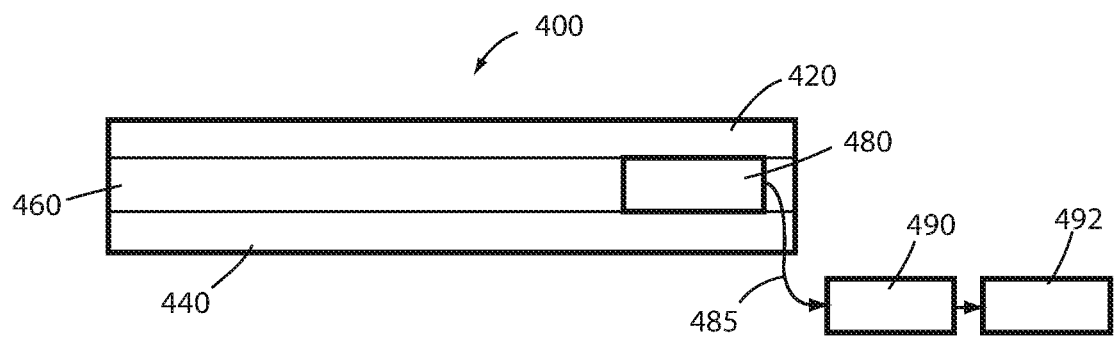
FIG. 6 is a schematic diagram of a three layer composite material including a detection device.

Referring to FIG. 6, the device 480 may be embedded in, or otherwise placed in, the intermediate layer 460 of the multiple layer composite material 400. The intermediate layer 460 may be positioned between the first fluid impermeable layer 420 and second fluid impermeable layer 440 as described herein. The device 480 may be a clock, timer, vibration sensor, motion detector, gyroscope, or hydrometer, for example, that is set or programmable to detect a particular number of time units, particular motion, or humidity level. The device 480 may communicate through a wire or cable 485 the count of time or movements to a receiver 490. The receiver 490 may include a separate or integrated display 492 to indicate the count and/or status of the composite material 400.

Figure 7:
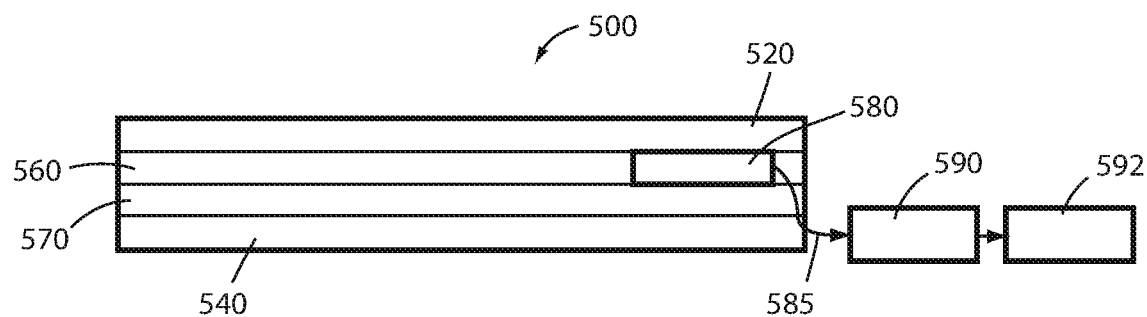
FIG. 7 is a schematic diagram of a four layer composite material including a detection device.

Similarly, if the composite material includes four layers, the device 580 may be embedded or positioned as shown in FIG. 7. The composite material 500 may include a first outer impermeable layer 520, a second outer impermeable layer 540, an inner fluid impermeable layer 560 with the device 580, and an inner reinforcement layer 570. As with the device 480, the device 580 may be a clock, timer, vibration sensor, motion detector, gyroscope, or hydrometer, for example, that is set or programmable to detect a particular number of time units, particular motion, or humidity level. The device 580 can communicate through a wire or cable 585 the count of time or movements to a receiver 590 and display component 592 to indicate the count and/or status of the composite material 500.

The devices 480, 580 may alternatively, communicate with the receiver 490, 590 wirelessly.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

Methods

Figure 8:
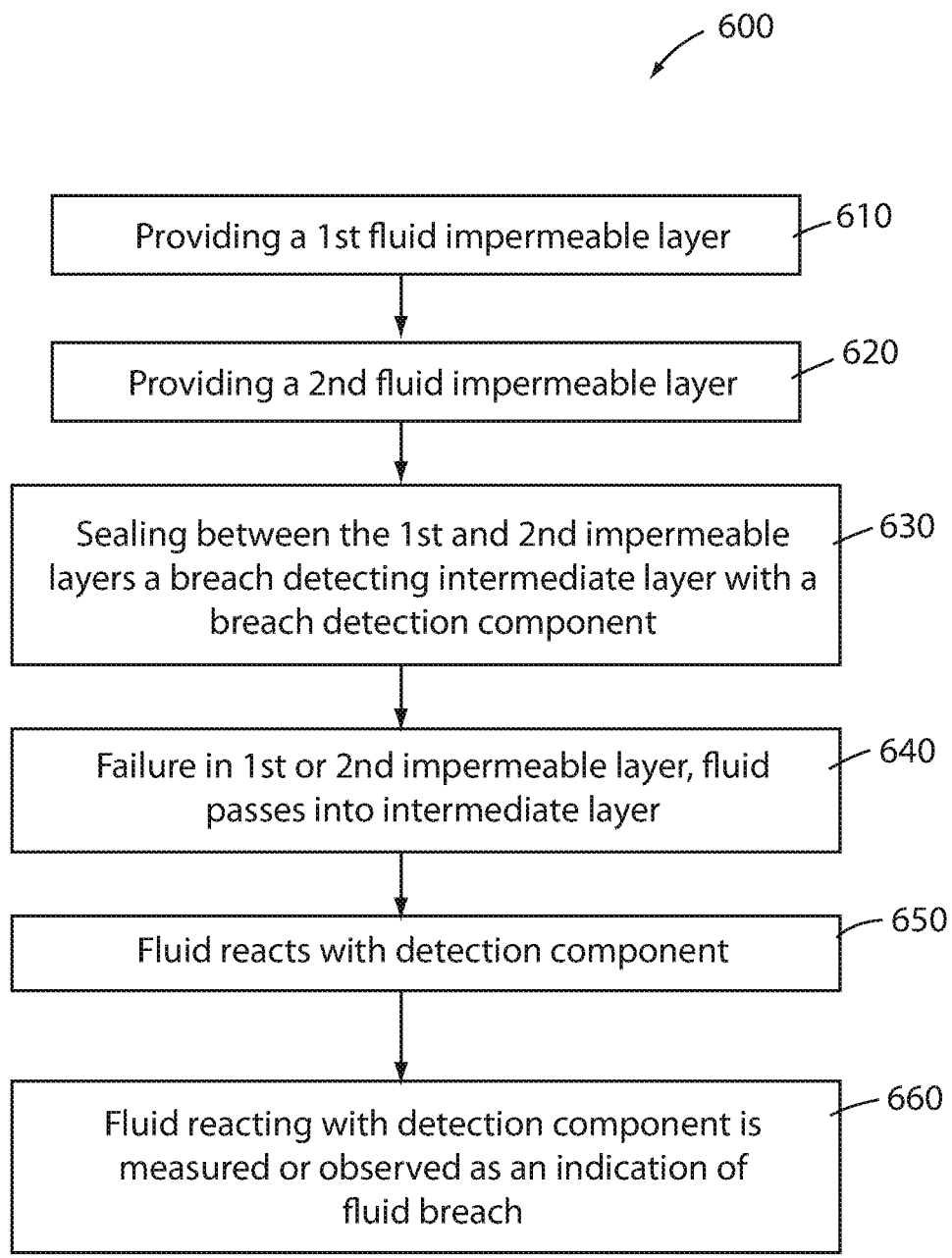
FIG. 8 is a flow diagram including the steps of a method for detecting a fluid breach in a multiple layer composite material.

In operation, detection of a fluid breach in the composite materials described above can be accomplished by the method 600 shown in FIG. 8. At step 610, the method includes providing a first fluid impermeable layer, at step 620 a second fluid impermeable layer is provided. An intermediate layer with a breach detection component is sealed between the first and second fluid impermeable layers at step 630, a failure occurring in the first or second fluid impermeable layer and fluid passing into the intermediate layer occurs at step 640, and the fluid reacts with the detection component at step 650. At step 650, the reaction is observed or measured as an indication of the fluid breach at step 660. The fluid breach into the intermediate layer may be detected while continuing to provide a fluid barrier presented by the intact second fluid impermeable layer.

Providing the breach detection component may include providing a reagent such as any of the reagents described herein including, but not limited to: a color changeable reagent capable of changing color based on one or more of: pKa values, the presence of fluids containing amino acids, proteins, urine, other bodily or biological fluids, or water. A breach detection component may also include a material having variable conductivity, a reagent capable of foaming after contact with the fluid, fibers with properties that are altered after contact with a fluid, reagents that produce or release a fragrance after contact with the fluid, and devices for measuring the age or wear of the material.

The step of observing a change in the breach detection components may include one or more of: observing a change in color of the reagent reacting with a fluid passing through the first fluid impermeable layer; observing the presence of a foam in the material after the reagent contacts the fluid; detecting a fragrance after the reagent contacts the fluid; detecting a change in a characteristic of a fiber after contact with the fluid; and reading a display device indicating the age and/or wear level of the material.

Figure 11:
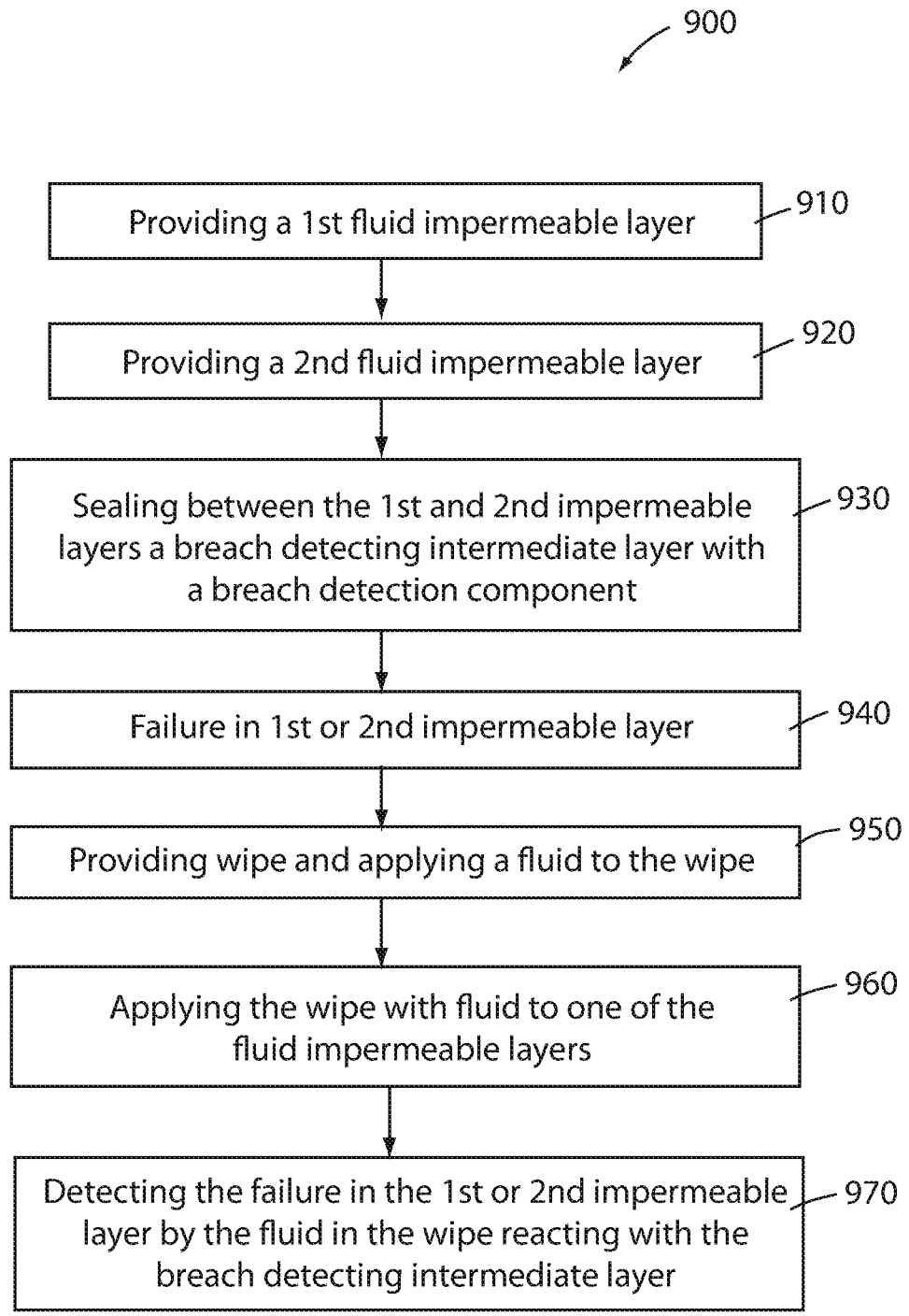
FIG. 11 is a flow diagram including the steps of another method for detecting a fluid breach in a multiple layer composite material.

Breach detection methods may also include wiping the outer surface of the multiple layer material and then detecting a failure of the outer layer. For example, the method 900 of FIG. 11 includes the step of providing a first fluid impermeable layer at step 910, providing a second fluid impermeable layer at step 920, sealing an intermediate layer with a breach detection component between the first and second impermeable layers at step 930, a failure occurring in one of the fluid impermeable layers at step 940, providing a wipe that is at least partially saturated with a fluid, or applying a fluid to the wipe at step 950, applying the wipe with the fluid to one of the fluid impermeable layers at step 960, and detecting the failure by the fluid reacting with the breach detecting intermediate layer at step 970. The fluid applied to the wipe may be water or an additional agent that is active with the reagent in the intermediate layer to detect a breach in the fluid impermeable layer.

Figure 9:
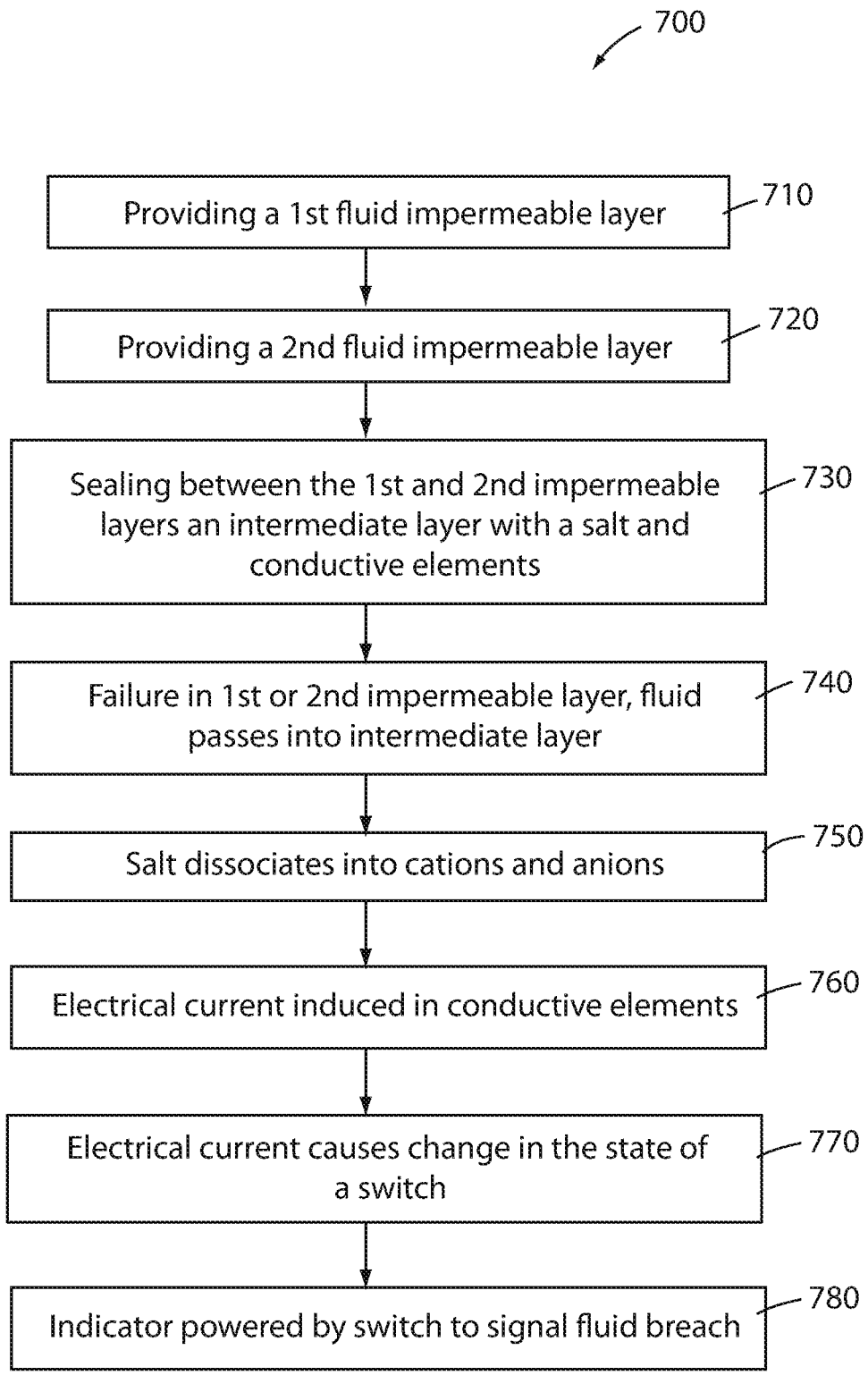
FIG. 9 is a flow diagram including the steps of a second method for detecting a fluid breach in a multiple layer composite material.

Additional steps may be included as shown in the method 700 of FIG. 9. After step 710 where there is provided a first fluid impermeable layer, and step 720 where there is provided a second fluid impermeable layer, there may be provided an intermediate layer with a salt and electric current source at step 730. A failure in the first or second fluid impermeable layer at step 740 causes the salt to dissociate into cations and anions at step 750, and conducts an electrical current in the electric circuit 760. The electrical current then powers an indicator to signal a fluid breach at step 780.

Further, a step 770 may be included to provide a switch operable to move between a first state and a second state, and powering a visible or audible indicator of the fluid contact with the electrolyte in the first state.

If the method includes the step of providing a detector as the breach detection component, the detector may be, for example, an interrogator or other device capable of sensing an electrical current when attached to terminals extending from the composite materials. The terminals, for example, can facilitate the flow of electric current in the presence of an electrolyte.

The step of providing a detector may also be the step of providing a timer, and the method may further include the step of measuring a length of time the material has been in use.

Additionally, or alternatively, the step of providing a detector can include providing a motion sensor. The method, then, may further include the steps of detecting a threshold level of movement of the material, associating the motion sensor with a counter, and counting a number of threshold level of movement of the material.

Once a set, or prescribed, number of threshold level movements is counted, the method may further include the steps of providing a communication component, communicating the number of threshold levels of movement to the communications component, and relaying the number of threshold level of movements to a display device.

Figure 10:
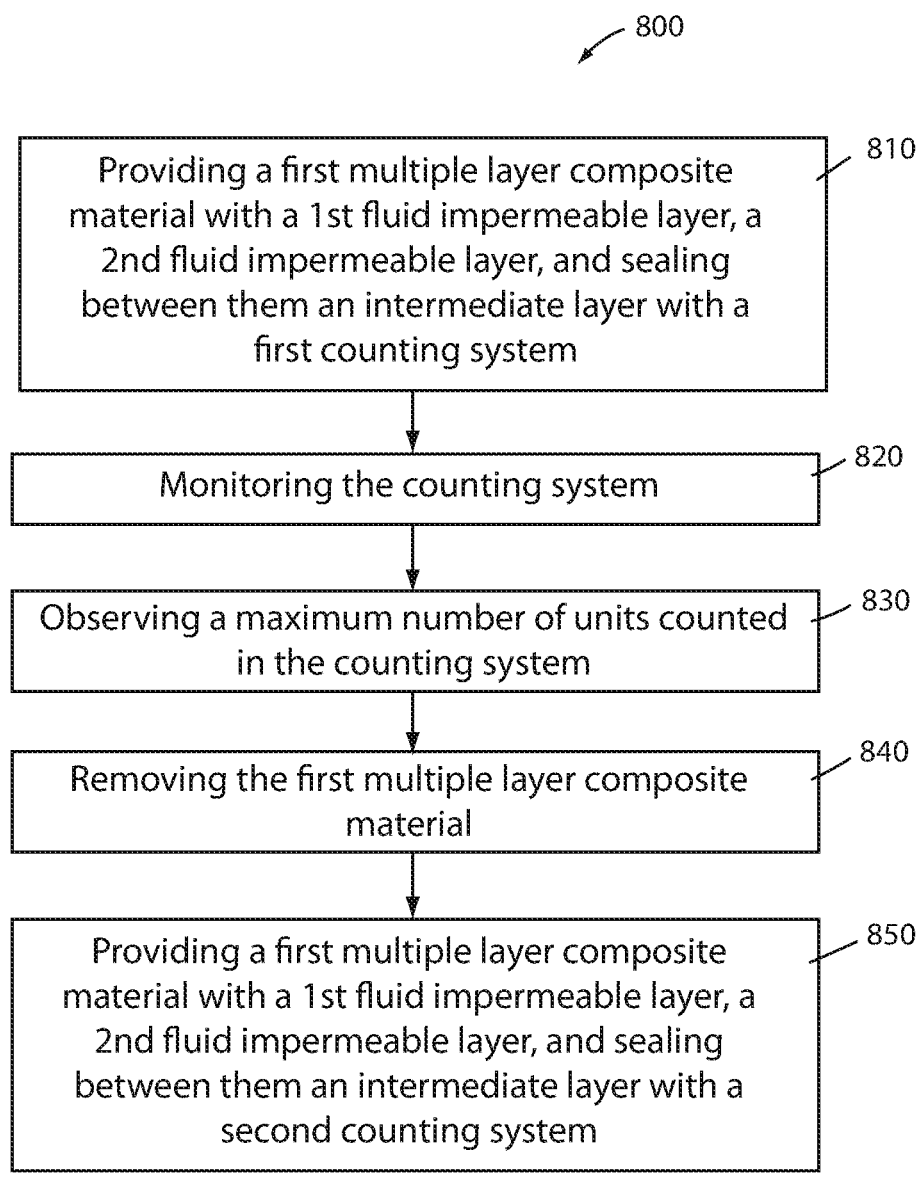
FIG. 10 is a flow diagram including steps of a third method for detecting a fluid breach in a multiple layer composite material.

For example, the method 800 shown in FIG. 10 includes the step of providing a first multiple layer composite material with a first fluid impermeable layer, a second impermeable, and sealing between them an intermediate layer with a first counting system at step 810, monitoring the counting system at step 820, observing a maximum number of units counted in the counting system at step 830, removing the first multiple layer composite material step 840, and providing a second multiple layer composite material with a first fluid impermeable layer, a second fluid impermeable layer, and sealing between them an intermediate layer with a second counting system at step 850.

Additional steps may be included, such as providing a display device for the displaying of the number of threshold level movements at the display device.

In order to facilitate the detecting, communicating, relaying and displaying steps, the method may also include providing a controller configured to control these steps.

The composite material described herein may be manufactured or constructed by the steps of providing a first fluid impermeable layer, providing a second fluid impermeable layer, providing an intermediate layer having a breach detector therein, and sealing the intermediate layer between the first and second fluid impermeable layers.

Construction or manufacturing methods for the composite material may also include the steps of providing a reagent as the breach detector, and further may include providing a material having variable conductivity as the breach detector or reagent.

If a material having variable conductivity is provided, the method of constructing or manufacturing the composite material may also include the step of providing a power source and a current detector.

Additionally, or alternatively, the construction or manufacturing method may include the step of providing the intermediate layer that includes providing an intermediate layer having fibers.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The embodiments of the invention in which an exclusive property or privilege is claimed are defined as follows:

1. A method of making a mattress cover for extending over and covering a mattress, the method comprising:
    providing a first fluid impermeable layer having a flexible fabric;
    providing a second fluid impermeable layer having a flexible fabric, at least one of the impermeable layers forming an outer surface of the mattress cover and being formed from a material to form the outer surface of the mattress cover with a cleanable surface, the cleanable surface configured to withstanding wiping and cleaning using a cleaning material wherein the mattress cover can be cleaned;
    sealing the first and second fluid impermeable layers together to form the mattress cover; and
    providing a breach detection component between the first and second fluid impermeable layers, wherein the breach detection component is configured to react with a fluid when the fluid passes through either of the first fluid impermeable layer or the second fluid impermeable layer when the first fluid impermeable layer or the second fluid impermeable layer has become fluid permeable to provide a visual or audible indication to a user a breach status of the first or second fluid impermeable layers.

2. The method according to claim 1, wherein said providing a breach detection component comprises providing a reagent between the first and second fluid impermeable layers, the reagent being reactive with the fluid when the fluid contacts the reagent after passing through the first or second fluid impermeable layer.

3. The method according to claim 2, further comprising providing an intermediate layer between the first and the second fluid impermeable layers, and wherein said providing a breach detection component comprises providing the reagent in the intermediate layer.

4. The method according to claim 2, wherein the first fluid impermeable layer is translucent, and wherein the reagent is visibly detectable when the fluid contacts the reagent.

5. The method according to claim 4, wherein providing the reagent includes providing a chemical reagent having a first color prior to contact with the fluid and a second color different from the first color after contact with the fluid, wherein the second color is visible through the first fluid impermeable layer.

6. The method according to claim 4, wherein providing the reagent includes providing a chemical reagent operable to produce a foam after contact with the fluid.

7. The method according to claim 2, further comprising providing an electrical circuit in communication with the reagent; and wherein providing the reagent includes providing a material of variable conductivity operable to induce an electrical current in the electrical circuit after contact with the fluid.

8. The method according to claim 7, further comprising providing the electrical circuit with a powered device wherein the powered device is powered when the reagent makes contact with the fluid.

9. The method according to claim 8, wherein said providing the electrical circuit with a powered device includes providing the electrical circuit with a powered device that generates a sound when powered.

10. The method according to claim 7, further comprising providing the electrical circuit with a pair of terminals for connection to a detector.

11. A method of detecting whether a breach occurs in a mattress cover, the method comprising the steps of:
    making a mattress cover according to the method of claim 1; and
    detecting a breach in at least one of the impermeable layers by detecting when a change in the breach detection component occurs.

12. The method according to claim 11, wherein the providing a breach detection component comprises providing a reagent between the first and second fluid impermeable layers, the reagent being reactive with the fluid when the fluid contacts the reagent after passing through the first or second fluid impermeable layer.

13. The method according to claim 12, further comprising providing an electrical circuit in communication with the reagent; and wherein providing the reagent includes providing a material that is a dielectric when in a dry state and an electrolyte when in contact with the fluid, wherein when the reagent contacts the fluid and is an electrolyte, the reagent inducing an electrical current in the circuit.

14. The method according to claim 13, further comprising providing the electrical circuit with a powered device and powering the powered device when the reagent makes contact with the fluid.

15. The method according to claim 14, further comprising providing the electrical circuit with a pair of terminals for connection to a detector, and connecting the pair of terminals to the detector to detect a breach status of the material.

16. The method according to claim 15, further comprising coupling the detector with a display device, and displaying a breach status of the material at the display.

17. The method according to claim 16, further comprising communicating the breach status detected by the detector to a bed control system.

* * * * *